United States Patent [19]

Kleemann et al.

[11] 4,254,269

[45] Mar. 3, 1981

[54] DITHIENYL BETA-HALOETHYL CARBINOLS

[75] Inventors: Axel Kleemann, Hanau; Ingomar Nubert; Fritz Stroman, both of Offenbach; Klaus Thiemer, Hanau, all of Fed. Rep. of Germany

[73] Assignee: Deutsche Gold- und Silber-Scheideanstalt vormals Roessler, Frankfurt, Fed. Rep. of Germany

[21] Appl. No.: 56,838

[22] Filed: Jul. 12, 1979

Related U.S. Application Data

[62] Division of Ser. No. 867,157, Jan. 5, 1978, Pat. No. 4,206,213.

[30] Foreign Application Priority Data

Jan. 12, 1977 [GB] United Kingdom ............... 1121/77

[51] Int. Cl.³ .......................................... C07D 333/12
[52] U.S. Cl. ................................. 549/59; 542/476; 544/405
[58] Field of Search .......................................... 549/59

[56] References Cited

U.S. PATENT DOCUMENTS

| | | | |
|---|---|---|---|
| 3,086,021 | 4/1963 | Biel | 549/59 |
| 3,766,173 | 10/1973 | Thiele et al. | 549/59 |
| 3,767,675 | 10/1973 | Posseli et al. | 549/59 |
| 4,175,088 | 11/1979 | Kleemann et al. | 549/59 |

FOREIGN PATENT DOCUMENTS

| | | | |
|---|---|---|---|
| 1462206 | 11/1966 | France | 549/59 |
| 683977 | 12/1952 | United Kingdom | 549/59 |

OTHER PUBLICATIONS

Robbs et al., "Chimie Therapeutique", No. 1, (1973), pp. 22–31.
Thiele et al., "Chem. Abstracts", vol. 77 (1972), p. 488.

*Primary Examiner*—Joseph E. Evans
*Attorney, Agent, or Firm*—Cushman, Darby & Cushman

[57] ABSTRACT

There are prepared compounds of the formula

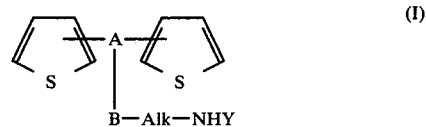

where $>A-B-$ has either the structure $>C(OH)-CH_2-$ or the structure $>C=CH$, Alk is a straight or branched chain $C_1-C_5$-alkylene group and Y is a $C_3-C_7$-cycloalkyl group, a benzyl group, a methylenedioxybenzyl group, a benzyl group having one, two or three $C_1-C_4$-alkyl or $C_1-C_4$-alkoxy group substituents, a $C_1-C_6$-alkyl group, or a $C_1-C_6$-alkyl group substituted by an amino group, a di $C_1-C_4$-alkylamino group, a mono $C_1-C_4$-alkyl-amino group, a morpholino group, a piperazino group or a 4-($C_1-C_4$-alkyl)-piperazino group, or Y is

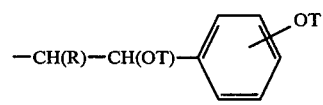

where R is hydrogen or a $C_1-C_4$-alkyl group and T is hydrogen or a $C_2-C_6$-alkanoyl group or where —NHY is

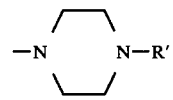

where R' is hydrogen, phenyl, phenyl substituted once or twice by $C_1-C_4$-alkyl groups, a $C_1-C_4$-alkoxy group or by halogen atoms, a $C_1-C_6$-alkyl group, a $C_1-C_4$-hydroxyalkyl group or a phenalkyl group whose alkyl portion consists of 1–4 carbon atoms or such a phenalkyl group containing 1 to 3 $C_1-C_4$-alkoxy group substituents or when Alk has 2 to 5 carbon atoms the group —NHY is a di-$C_1-C_4$-alkylamino group or the group —NH—CH(R)—CH(OH)—$C_6H_5$ and salts thereof. The compounds are effective in improving peripheral and cerebral circulation. There are also produced intermediate compounds of formula (II) where NHY is replaced by chlorine, bromine or iodine.

2 Claims, No Drawings

DITHIENYL BETA-HALOETHYL CARBINOLS

This is a division of application Ser. No. 867,157, filed Jan. 5, 1978, now U.S. Pat. No. 4,206,213.

BACKGROUND OF THE INVENTION

Compounds corresponding to the general formula

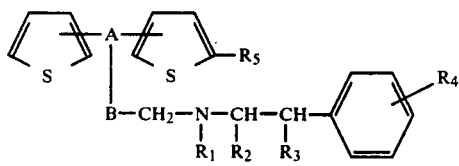

in which $R_1$, $R_2$ and $R_5$ each represent a hydrogen atom or a methyl group, $R_3$ represents a hydrogen atom or a hydroxyl group, $R_4$ represents a hydrogen or chlorine or fluorine atom or a trifluoromethyl group or an alkyl group with 1 to 6 carbon atoms or an alkoxy group with 1 to 6 carbon atoms and the bridge member >A—B— has the structure >C(OH)—CH$_2$— or >C=CH—, are already known. They are particularly effective in improving cerebral circulation.

These compounds can be produced by a process in which a compound corresponding to the general formula

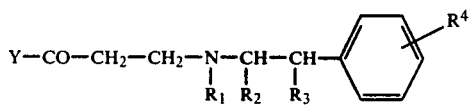

in which Y is chlorine or bromine or an alkoxy group or a thienyl radical, is reacted with a thienyl metal compound (thienyl lithium, thienyl Grignard compound) and compounds of the general formula in which >A—B— is the group >C(OH)—CH$_2$—, are optionally converted with a dehydrating agent into the corresponding unsaturated compounds (>A—B—: >C=CH—) by known methods and the basic compounds obtained are optionally converted into the salts by known methods (Thiele German Pat. No. 1,921,453 and related but not identical Thiele U.S. Pat. No. 3,766,173. The entire disclosure of the Thiele U.S. patent is hereby incorporated by reference and relied upon.).

However, it is not possible by this process to produce any compounds in which the phenyl radical in the above formula is substituted by a hydroxy group or in which the amine portion is derived from structurally different amines.

Furthermore, there are known compounds of the following formula

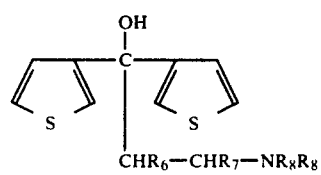

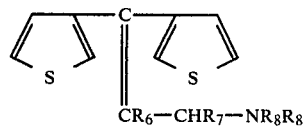

In the just given formulae $R_6$ and $R_7$ represent hydrogen or a methyl group and both $R_8$ are, $C_1$-$C_4$-alkyl groups or one $R_8$ is hydrogen and the other is a benzyl group or the entire group —NR$_8$R$_8$ forms a pyrrolidino group, a piperidino group, a morpholino group or a homopiperidino group. There is stated as the main activity for these compounds a spasmolytic activity (Chimie Therapeutique (1973) pages 22–31).

SUMMARY OF THE INVENTION

The invention is directed to other new compounds of the formula

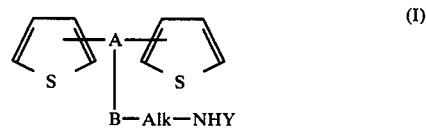

(I)

where >A—B— has either the structure >C(OH)—CH$_2$— or the structure >C=CH, Alk is a straight or branched chain $C_1$-$C_5$-alkylene group and Y is a $C_3$-$C_7$-cycloalkyl group, a benzyl group, a methylenedioxybenzyl group, a benzyl group having one, two or three $C_1$-$C_4$-alkyl or $C_1$-$C_4$-alkoxy group substituents, a $C_1$-$C_6$-alkyl group, or a $C_1$-$C_6$-alkyl group substituted by an amino group, a di $C_1$-$C_4$-alkylamino group, a mono $C_1$-$C_4$-alkylamino group, a morpholino group, a piperazino group or a 4-($C_1$-$C_4$-alkyl)-piperazino group, or Y is

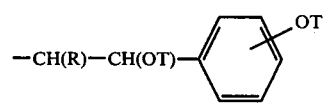

where R is hydrogen or a $C_1$-$C_4$-alkyl group and T is hydrogen or a $C_2$-$C_6$-alkanoyl group (e.g., acetyl, propionyl, hexanoyl) or where —NHY is

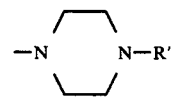

where R' is hydrogen, phenyl, phenyl substituted once or twice by $C_1$-$C_4$-alkyl groups, a $C_1$-$C_4$-alkoxy group or by halogen atoms (e.g., fluorine, chlorine or bromine), a $C_1$-$C_6$-alkyl group, a $C_1$-$C_4$-hydroxyalkyl group or a phenalkyl group whose alkyl portion consists of 1-4 carbon atoms or such a phenalkyl group containing 1 to 3 $C_1$-$C_4$-alkoxy group substituents or wherein the group —NHY is morpholino, piperidino or when Alk has 2 to 5 carbon atoms a di-$C_1$-$C_4$-alkylamino group or the group —NH—CH(R)—CH(OH)—$C_6$H$_5$ and salts thereof, preferably a pharmaceutically acceptable salt.

The two thienyl radicals are preferably attached to A—B— in the same portion (bis-thienyl-(3) or bis-thienyl-(2) derivatives). However, it is also possible that A—B— is simultaneously attached to a thienyl-(2) and a thienyl-(3) group. The group R in the structural part

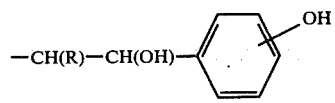

is preferably methyl or ethyl. The hydroxy group on the phenyl ring can be in the ortho, para or meta position. In case this is acylated the starting $C_2$-$C_6$ aliphatic carboxylic acid can be straight or branched and especially can consist of 2–4 carbon atoms, e.g., acetyl, propionyl, butyryl, isobutyryl. The alkylene chain Alk is preferably straight and preferably consists of 1, 2 or 3 carbon atoms.

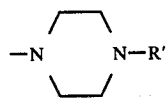

where R' is as defined above; preferably R' is phenyl or a phenyl substituted by a $C_1$-$C_2$-alkyl group (for example methyl or ethyl) or a $C_1$-$C_2$-alkoxy group ($OCH_3$, $OC_2H_5$). Preferably the substituent is in the ortho position. In case R' is a phenalkyl group, it is especially the benzyl or phenethyl group, in a given case substituted by 1 or 2 methoxy groups.

In addition to the compounds set forth in the working examples below, other illustrative examples of compounds within the invention include
[1,1-(dithienyl-(3)-1-hydroxyamyl-(5)]-[1-hydroxy-1-(p-hydroxyphenyl)-propyl-(2)]-amine;
[1,1-dithienyl-(2)-1-hydroxypropyl-(3)]-[1-hydroxy-1-(p-hydroxyphenyl)-propyl-(2)]-amine;
[1,1-dithienyl-(2)-1-propenyl-(3)]-[1-hydroxy-1-(p-hydroxyphenyl)-propyl-(2)]-amine
as well as compounds of the formula

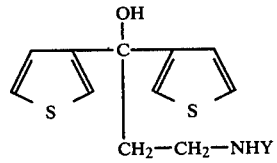

in the following table

—NHY
—NH—cycloheptyl

—NH—CH₂—⟨phenyl⟩

—NH—CH₂—⟨phenyl⟩—CH₃

—NH—CH₂—⟨phenyl⟩—C₄H₉

—NH—CH₂—⟨phenyl(CH₃)⟩—CH₃

-continued

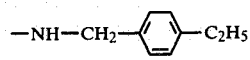

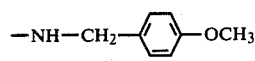

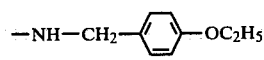

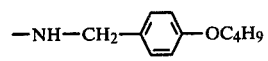

—NHC₆H₁₃

—NH—CH₂CH₂NH₂

—NH—CH₂NH₂

—NH—CH₂CH₂NH₂

—NH(CH₂)₆NH₂

—NH(CH₂)₃NHCH₃

—NH(CH₂)₃NHC₂H₅

—NH(CH₂)₄NHC₄H₉

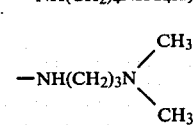

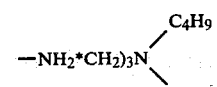

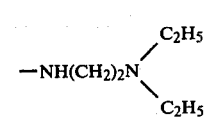

—NH(CH₂)₂NHi-C₃H₇

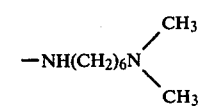

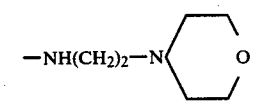

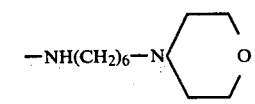

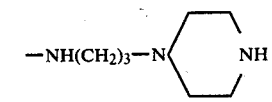

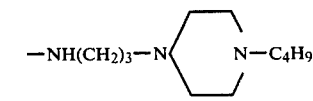

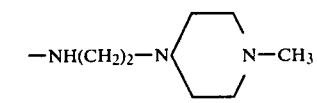

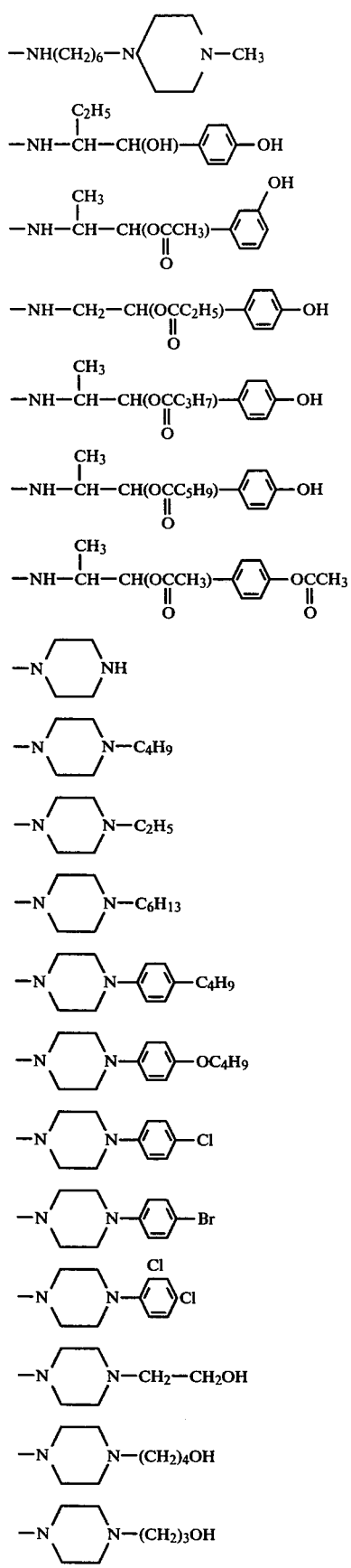

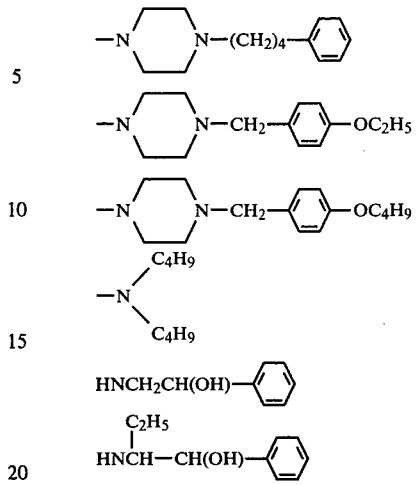

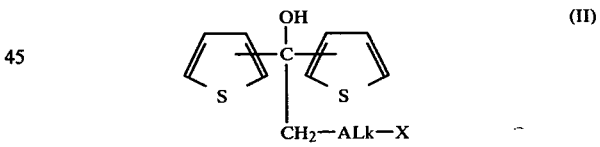

While the compounds in the above table and in examples 1-7 are bis-thienyl-(3) derivatives, the corresponding bis-thienyl-(2) derivatives can be made simply by replacing the 3-bromo-thiophene by 2-bromo-thiophene in the starting material as pointed out hereinafter and as shown in Thiele German Pat. No. 1,921,453.

The new compounds according to the invention of formula (I) show pharmacodynamic activity, especially in disorders of the heart and circulation system. In particular, they produce an increase in peripheral and cerebral circulation and in this respect, for example, are considerably more active, especially in regard to peripheral circulation, than the known compounds according to Thiele German Pat. No. 1,921,453. In some cases, the compounds according to the invention also dilate the coronary arteries and increase the power of the heart.

The compounds of general formula (I) are produced by condensing a compound corresponding to the general formula $$\begin{array}{c} \text{OH} \\ | \\ \underset{S}{\diagup}\!\!\!\!\diagdown\!\!-\!\!\underset{|}{C}\!\!-\!\!\underset{S}{\diagup}\!\!\!\!\diagdown \\ | \\ CH_2-ALk-X \end{array}$$ (II)

in which Alk is a straight or branched chain $C_1$-$C_5$-alkylene group and X represents chlorine, bromine or iodine, with an amine corresponding to the general formula $H_2NY$ (III)

in which Y is as defined above, and optionally converting compounds corresponding to general formula (I), in which $>A-B-=>C(OH)-CH_2-$, into the corresponding unsaturated compounds ($>A-B-=>C=CH-$) with a dehydrating agent by known methods and/or acylating with an aliphatic (e.g., alkanoic) $C_2$-$C_6$ carboxylic acid and optionally producing the salts from the basic compounds obtained.

This condensation reaction is carried out, for example, in the presence or absence of a solvent and at a temperature in the range from 0° to +150° C. and preferably at a temperature in the range from 20° to 100° C.

Suitable inert solvents or suspending agents are, for example, saturated ethers, such as lower aliphatic dialkyl ethers, e.g., diethyl ether, dipropyl ether, dibutyl ether, alkyl ethers of cycloalkanols and alkyl-substituted cycloalkanols, e.g., methyl cyclohexyl ether, ethyl cyclohexyl ether; saturated liquid hydrocarbons, e.g., pentane, hexane, octane, decane, petroleum ether, saturated cycloaliphatic hydrocarbons which may even be substituted by lower alkyl radicals, e.g., cyclohexane, decahydronaphthalene, methyl cyclohexane, cyclic ethers, such as tetrahydrofuran and dioxane; benzene; alkyl benzenes such as toluene and xylene; aliphatic saturated ketones, e.g., acetone, methyl ethyl ketone; aliphatic and cycloaliphatic alcohols, e.g., methyl alcohol, ethyl alcohol, isopropyl alcohol, butyl alcohol, cyclohexanol. The concentration of compound II in the solvent or suspending agent amounts for example to between 10 and 50%. The condensation reaction with compound III is best carried out in the presence of a base or hydrogen halide acceptor, such as, for example, tertiary amines (e.g., triethylamine, dimethyl aniline, tributyl amine), alkali metal carbonates (potash or sodium carbonate), alkali metal hydroxides, e.g., sodium hydroxide, potassium hydroxide. It is even possible to use compound III itself as hydrogen halide acceptor. The condensation reaction takes place with advantage in a stoichiometric ratio, although it is also possible to use any excess of compound III. The reaction time is governed by the reaction temperature. At temperatures in the range from 100° to 120° C. for example, the reaction is over in 4 to 12 hours.

The elimination of water from compounds corresponding to general formula (I), in which >A—B—=>C(OH)—CH$_2$—, is best carried out at elevated temperatures, for example, at a temperature in the range from 20° to 150° C. It is preferred to use a solvent such as, for example, dialkyl ethers (such as those mentioned above), dioxane, glacial acetic acid, benzene, toluene, ethanol, isopropanol and so on.

For carrying out this dehydrating reaction, there is no need initially to isolate the compound of formula (I), in which >A—B— represents the group >C(OH)—CH$_2$—, instead the reaction mixture obtained after the reaction of compound II with compound III may for example be directly treated with the dehydrating agent, optionally after removal of the solvent. For example, isopropanolic or ethanolic hydrochloric acid may be directly added to the reaction mixture which is then heated for a few minutes to boiling point to obtain dehydration. The reaction product may be worked up in the usual way.

Suitable dehydrating agents are, for example, mineral acids such as sulfuric acid or hydrohalic acids, e.g., hydrochloric acid or hydrobromic acid; organic acids, such as oxalic acid, formic acid, thionyl chloride; aluminum chloride; zinc chloride; tin chloride; boron trifluoride; potassium hydrogen sulfate; phosphorus pentoxide; acid chlorides, e.g., acetyl chloride; red phosphorus-iodine in the presence of water.

If compounds having the structural part

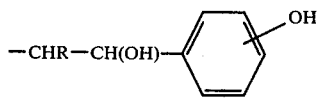

are to be obtained then optionally the hydroxy group on the phenyl ring can be subsequently acylated by a C$_2$-C$_6$ alkanoyl group.

The acylation can take place in an inert solvent or suspension agent such as dioxane, dimethyl formamide, benzene or toluene at temperatures between 0° and 200° C. As acylating agents there can be used aliphatic C$_2$-C$_6$ ketenes (e.g., ketene, methyl ketene, ethyl ketene, diethyl ketene) as well as acid halides, acid anhydrides or acid esters of aliphatic carboxylic acid (e.g., alkanoic acids) of 2 to 6 carbon atoms, e.g., acetyl chloride, acetyl bromide, propionyl chloride, butyryl chloride, hexanoul chloride, acetic anhydride, butyric anhydride, optionally with an acid binding agent such as potassium carbonate, sodium carbonate or sodium ethylate or a tertiary amine, for example, triethyl amine. With the esters there are particularly employed those with lower aliphatic alcohols, e.g., methyl acetate, ethyl acetate, butyl acetate, methyl propionate, methyl caproate. In the acylation it is also possible to proceed by first producing an alkali compound from the reacting compound of formula (I) having the hydroxyl group on the phenyl ring while it is reacted at a temperature between 0° and 150° C. with an alkali metal, alkali hydride or alkali amide (particularly sodium ot sodium compounds, e.g., sodium hydride, sodium amide) in an inert solvent such as dioxane, dimethyl formamide, benzene or toluene and then to add the acylating agent.

In place of the mentioned acylating agents there can also be used other chemically equivalent acylating agents (see for example also: L. F. and Mary Fieser, "Reagents for Organic Synthesis," John Wiley and Sons, Inc., New York, 1967, Vol. 1, pages 1303-4 and Vol. 2 page 471). It is understood that acyl groups present in formula (I) also can again be split off in known manner, for example, by hydrolysis in the presence of acids, e.g., hydrochloric acid or sulfuric acid or basic materials, e.g., sodium hydroxide or potassium hydroxide, at a temperature between 20° and 150° C.

Those compounds which contain asymmetrical carbon atoms and which are generally formed as racemates may be split up into the optically active isomers by methods known per se, for example, by means of an optically active acid. However, it is also possible to use optically active or even diastereomeric starting materials of general formula (III) from the outset, in which case a corresponding pure optically active form or diastereomeric configuration is obtained as the end product.

In the case of amines of the formula H$_2$N—CH(-R)—CH(OH)C$_6$H$_5$ which also can be substituted in the phenyl ring by hydroxy or C$_2$-C$_6$ alkanoyloxy there can be used as starting materials those which are present in the erythro or threo configuration. The end products of formula (I) are obtained in free form or in the form of their salts, depending upon the process conditions and starting materials used. The salts of the end products may be converted back into the bases by methods known per se, for example, with alkali (e.g., sodium hydroxide or potassium hydroxide) or ion exchangers, e.g., anion exchange resins. Salts may be obtained from the bases by reaction with organic or inorganic acids, especially those which are suitable for the formation of therapeutically valuable salts. Acids such as these are, for example, hydrohalic acids, e.g., hydrochloric acid, hydrobromic acid, sulfuric acid, acids of phosphorus, e.g., phosphoric acid, phosphorous acid, nitric acid, perchloric acid, organic mono, di- or tri-carboxylic acids of the aliphatic, alicyclic, aromatic or heterocyclic series, also sulfonic acids. Examples of these acids are formic acid, acetic acid, propionic acid, butyric acid, succinic acid, oxalic acid, malonic acid, glycolic acid, lactic acid, malic acid, tartaric acid, citric acid, ascorbic acid, maleic acid, fumaric acid, hydroxy maleic acid or pyruvic acid; phenyl acetic acid, benzoic acid, salicylic acid or p-amino salicylic acid, embonic acid, methane sulfonic acid, ethane sulfonic acid, hydroxyethane sulfonic acid, ethylene sulfonic acid; halogen benzene sulfonic acid, e.g., p-chlorobenzenesulfonic acid, toluene sulfonic acid, naphthalene sulfonic acid or sulfanilic acid.

The compounds according to the invention are suitable for the production of pharmaceutical compositions and preparations. The pharmaceutical compositions contain as active principle one or more of the compounds according to the invention, optionally in admixture with other pharmacologically active substances. The medicaments may be produced with the usual pharmaceutical excipients and additives. The medicaments may be administered enterally, parenterally, orally, perlingually or in the form of sprays. They may be made up in the form of tablets, capsules, pills, dragees, suppositories, liquids or aerosols. Suitable liquids are, for example, oily or aqueous solutions or suspensions.

The starting compounds of formula (II) are also new and, according to the invention, are obtained by reacting thien-(3)-yl or thien-(2)-yl lithium with a compound corresponding to the formula

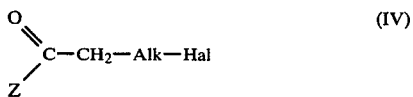

in which Alk is a straight or branched $C_1$-$C_5$ alkylene group, preferably a straight chain $C_1$-$C_3$-alkylene group and Z is a lower alkoxy group, e.g., 1-6 carbon atoms, chlorine, bromine, iodine or a thienyl radical, in an inert medium at a low temperature, preferably below $-50°$ C. The compound of formula (II) is formed in a yield of, for example, 96% of the theoretical.

By contrast, hitherto known reactions of this type, for example of thien-(3)-yl lithium with ω-phenylethylaminopropionic acid esters (see German Pat. Specification No. 1,921,453) do not take place uniformly and the required dithien-(3)-yl compound can only be isolated in yields of at most 30%. In particular, other thienyl isomers are always formed in relatively large quantities. In addition, separation of the required dithienyl compound from the other reaction products and its purification are extremely difficult and can only be carried out, for example, by complicated and elaborate recrystallization several times in combination with treatment with active carbon.

In general formula (IV), the radical Z is in particular a saturated aliphatic alkoxy group with 1 to 6 carbon atoms, preferably with 1 to 4 carbon atoms, which may even be branched, chlorine or bromine. However, Z can also be a thien-(2)-yl radical or a thien-(3)-yl radical.

The reaction of the thienyllithium compound, especially thien-(3)-yl lithium, with compound IV takes place in an inert liquid solvent mixture which preferably consists of a saturated ether and a saturated hydrocarbon and/or a benzene mono-substituted by $C_1$-$C_3$-alkyl radicals.

If the solvent mixture consists of an ether and a saturated hydrocarbon, from 0.3 to 3 parts by volume and preferably from 0.8 to 3 parts by volume of ether are used for example to 1 part by volume of hydrocarbon. If the solvent mixture consists of ether and monoalkyl benzene, from 0.1 to 3 parts by volume and preferably from 0.2 to 1 part by volume of ether are used for example to 1 part by volume of alkyl benzene. If the solvent mixture at most 30%, in particular, other thienyl isomers are always formed in relatively large quantities. In addition, separation of the required dithienyl compound from the other reaction products and its purification are extremely difficult and can only be carried out, for example, by complicated and elaborate recrystallization several times in combination with treatment with active carbon.

In general formula (IV), the radical Z is in particular a saturated aliphatic alkoxy group with 1 to 6 carbon atoms, preferably with 1 to 4 carbon atoms, which may even be branched, chlorine or bromine. However, Z can also be a thien-(2)-yl radical or a thien-(3)-yl radical.

The reaction of the thienyllithium compound, especially thien-(3)-yl lithium, with the halogen $C_2$-$C_6$-alkane carboxylic acid ester takes place at temperatures below $-50°$ C. in an inert liquid solvent mixture which preferably consists of a saturated ether and a saturated hydrocarbon and/or a benzene preferably from 0.8 to 3 parts by volume of ether are used for example to 1 part by volume of hydrocarbon. If the solvent mixture consists of ether and monoalkyl benzene, from 0.1 to 3 parts by volume and preferably from 0.2 to 1 part by volume of ether are used for example to 1 part by volume of alkyl benzene. If the solvent mixture consists of the three components ether, saturated hydrocarbon and alkyl benzene, the ratio in which the three components ether, hydrocarbon and benzene are mixed is, for example, 0.1–0.9:0.1–0.9:0.1–0.9. Suitable saturated ethers are, in particular, aliphatic symmetrical or asymmetrical dialkyl ethers, the alkyl groups preferably consisting of 1 to 6 carbon atoms and being, for example, methyl, ethyl, isopropyl, propyl, isobutyl or butyl. Other suitable ethers are, for example, $C_1$-$C_6$-alkyl ethers of saturated cycloalkanols and the alkyl-substituted cycloalkanols, the cycloalkanol rings each consisting of 3, 4, 5 or 6 carbon atoms. The ethers are preferably liquid at temperatures in the range from $-80°$ to $+20°$ C.

The saturated hydrocarbons are aliphatic or cycloaliphatic hydrocarbons which are liquid at temperatures in the range from $-80°$ to $+20°$ C. and which may contain for example from 5 to 9 and preferably 6 or 7 carbon atoms and may even be branched. The cycloaliphatic hydrocarbons are preferably substituted once or even several times (twice, three times) by $C_1$-$C_4$-alkyl radicals, especially methyl, ethyl mono-substituted by $C_1$-$C_3$-alkyl radicals.

As halogenated carboxylic acid esters there can be used, for example, β-halogen propionic acid esters, ν-halogen butyric acid esters, Δ-halogen valeric acid esters, ε-halogen caproic acid esters, ω-halogen heptanoic acid esters.

In general formula (IV) above, the radical R represents in particular a saturated aliphatic alkyl group which 1 to 6 carbon atoms, preferably with 1 to 4 carbon atoms, which may also be branched. Hal is preferably chlorine or bromine.

Examples of compounds of formula (IV) are ethyl 3-bromopropionate (3-bromopropionic acid ethyl ester), methyl 3-bromopropionate, propyl 3-bromopropionate, isopropyl 3-bromopropionate, butyl 3-bromopropionate, hexyl 3-bromopropionate, amyl 3-bromopropionate, methyl 3-chloropropionate, ethyl 3-chloropropionate, propyl 3-chloropropionate, isopeopyl 3-bromopropionate, butyl 3-chloropropionate, sec.butyl 3-bromopropionate, hexyl 3-chloropropionate, methyl 3-iodopropionate, ethyl 3-iodopropionate, propyl 3-iodopropionate, butyl 3-iodopropionate, ethyl 4-chlorobutyrate, methyl 4-bromobutyrate, ethyl 5-bromovalerate, methyl 5-chlorovalerate, ethyl 5-chlorocaproate, methyl 5-bromocaproate, ethyl 5-bromoheptanoate, methyl 5-chloroheptanoate.

If the solvent mixture consists of an ether and a saturated hydrocarbon, from 0.3 to 3 parts by volume and or propyl radicals, the number of ring atoms amounting to 3, 4, 5, 6 or 7. The saturated alkyl radicals which may be used as substituents for the benzene are methyl, ethyl, propyl, isopropyl, butyl, isobutyl, tert.-butyl, 1-methyl propyl.

Examples of the solvents which may be used are diethyl ether, diisopropyl ether, methyl cyclopentyl ether, hexane, cyclohexane, toluene, xylene, methyl cyclohexane, methyl cyclopentane, ethyl cyclohexane, dimethyl cyclohexane, methyl propyl ether, ethyl propyl ether, dimethyl ether, dihexyl ether, diamyl ether, dibutyl ether, dipropyl ether, diisobutyl ether, ethyl cyclohexyl ether, ethyl cyclopropyl ether, methyl cyclobutyl ether, methyl ethyl cyclohexyl ether, ethyl methyl cyclohexyl ether, pentane, nonane, isoheptane, isooctane, octane, 2,3-dimethyl pentane, cyclopentane, ethyl cyclopropane, methyl cycloheptane, butyl cyclohexane, isopropyl cyclohexane, trimethyl cyclohexane, diethyl cyclopentane, isopropyl benzene, propyl benzene, butyl benzene, sec.butyl benzene, dibutyl benzene, dipropyl benzene.

It is of advantage to add compound IV (particularly if it is a $\beta$-halogen alkanoic acid ester, e.g., $\beta$-halogen propionic acid ester) as such or in the form of a solution in the hydrocarbon and/or ether (for example diisopropyl ether and/or toluene) to the thienyl lithium such as thien-(3)-yl lithium precooled to the reaction temperature and then to keep the reaction mixture at the reaction temperature for about 1 to 4 hours. Thereafter water for example is added to the reaction solution, optionally after heating to $-20°$ to $+20°$ C. The organic phase is dried (e.g., using $MgSO_4$ or $NaSO_4$) and concentrated by evaporation under reduced pressure. The crude 1,1-bis-[thien-(3 or 2)-yl]-3-halogen alkanol (e.g., propanol) thus obtained may be used without further purification for the reaction with the amine $NH_2Y$. The thienyl lithium compound, for example, thien-(3 or 2)-yl lithium is generally produced beforehand from 2-bromo or 3-bromothiophene or from 2-iodo or 3-iodothiophene in the ether and a $C_1$–$C_5$-alkyl lithium or aryl lithium compound in the ether/hydrocarbon mixture, the ethers and hydrocarbons already mentioned (including the alkyl benzenes) being suitable for this purpose (a dialkyl ether being particularly preferred as the ether component). The alkyl radical of the alkyl lithium compound may be linear or branched. Examples of suitable alkyl lithium compounds are butyl lithium, sec.-butyl lithium, tert.-butyl lithium, methyl lithium, ethyl lithium, phenyl lithium, naphthyl lithium. The concentration of the alkyl or aryl lithium compound in the particular solvent used amounts for example to from 5 to 30% by weight. The concentration of the bromothiophene or iodothiophene in the particular solvent amounts for example to from 10 to 100% by weight.

In general, the bromothiophene or iodothiophene, either as such or in the form of a solution in the ether or liquid aliphatic hydrocarbon or the alkyl benzene, is added to the lithium alkyl or lithium aryl, which is dissolved or suspended in one of the above-mentioned ethers or a mixture of ether and aliphatic hydrocarbon in a volume ratio of 1–1.5:1 or ether and alkylbenzene in a volume ratio of 0.2–0.5:1 (concentration of the lithium compound from 5 to 30% by weight) and cooled to a temperature below $-70°$ C., in such a way that the temperature does not exceed $-70°$ C. The reaction component of formula (IV) is then added, for example, in the form of a 10 to 100% solution (% by weight) in one of the above-mentioned dialkyl ethers or alkyl benzenes, again in such a way that the temperature does not exceed $-70°$ C.

In one preferred embodiment of the process according to the invention, the reaction is carried out in a solvent mixture of toluene and diisopropyl ether and, after the reaction mixture has been hydrolyzed, the organic phase is subjected to a fractional vacuum distillation, the low-boiling constituents of the mixture, such as for example diisopropyl ether, thiophene, butyl bromide, etc., together with some of the toluene used being removed overhead, whilst a solution of 1,1-bis-[thien-(3) and/or thien-(2)-yl]-$\omega$-halogen propanol in toluene is recovered as sump residue and is directly introduced into the next stage of the process.

The reactants may be used for example in the following molar ratios: thien-(3)-yl lithium:compound II = 2.0–4.0:1.

Based on lithium alkyl and bromo- or iodothiophene, the following molar ratio for example may be applied: alkyl lithium compound:3-bromo(iodo)thiophene:compound II = 2.5–5.0:2.0–4.0:1, more especially 2.0–5.0:2.0–4.0:1.

The reaction temperature, for example, should not exceed $-50°$ C. It is of advantage to carry out the reaction at a temperature of from $-65°$ C. to $-75°$ C., the reaction preferably being carried out at a temperature below $-70°$ C., for example at a temperature of from $-80°$ C. to $-70°$ C.

The 1,1-bis-[thien-(3 and/or 2)-yl]-$\omega$-halogen propanol of formula (II) thus obtained may then be reacted with compound III directly, i.e., without further purification. This reaction may be carried out in the presence or absence of solvent or suspending agent. Suitable inert solvents or suspending agents are, for example, the same solvents or suspending agents which are used for the reaction of the thienyl lithium with compound IV, for example diisopropyl ether, toluene and the like. In addition, it is also possible for example to use other alkyl and dialkyl benzenes, dialkyl ethers, aliphatic ketones, e.g., acetone, methyl ethyl ketone, methyl butyl ketone, diethyl ketone and other dialkyl ketones, and aliphatic and cycloaliphatic alcohols, e.g., alkanols and cycloalkanols such as methanol, ethanol, isopropanol, propanol, butanol, hexanol, cyclohexanol.

It is also possible directly to react the reaction mixture, in which the compound of formula (II) is formed, with compound III. Since a reaction mixture such as this still contains the alkyl halide formed during the reaction, it may be necessary to use a corresponding excess of compound III.

The derivatives obtained from the intermediate compound of formula (II) produced in accordance with the invention are substantially isomer-free and are obtained in satisfactorily pure form after a single recrystallization.

The compounds according to the invention are suitable for the production of pharmaceutical compositions and preparations. The pharmaceutical compositions or medicaments contain, as active principle, one or more of the compounds according to the invention, optionally in admixture with other pharmacologically or pharmaceutically active substances. The medicaments may be prepared with the usual pharmaceutical excipients, assistants, carriers and diluents.

As carriers and assistants, for example, are those recommended in the following literature as adjuvants for pharmacy, cosmetic and related fields such as in Ullmann's Encyklopüdie der technischer Chemie, Vol. 4 (1953), pages 1 to 39; Journal of Pharmaceutical Sciences 52 (1963), pages 918 et seq.; N. v. Czetsch-Lindenwald, Hilftstoffe für Pharmazie und angrenzende Gebiete; Pharm. Ind. 2 (1961), pages 72 et seq.; Dr. H. P. Fiedler, Lexicon der Hilftstoffe für Pharmazie, Kosmetik und angrenzende Gebiete, Cantor Kg. Aulendorf i. Wurtt (1971).

Examples of such materials include gelatin, natural sugars such as sucrose or lactose, lecithin, pectin, starch (for example cornstarch), alginic acid, tylose, talc, lycopodium, silica (for example colloidal silica), glucose, cellulose, cellulose derivatives for example cellulose ethers in which the cellulose hydroxyl groups are partially etherified with lower aliphatic alcohols and/or lower saturated oxyalcohols (for example, methyl hydroxypropyl cellulose, methyl cellulose, hydroxyethyl cellulose), stearates, e.g., methylstearate and glyceryl stearate, magnesium and calcium salts of fatty acids with 12 to 22 carbon atoms, especially saturated acids (for example calcium stearate, calcium laurate, magnesium oleate, calcium palmitate, calcium behenate and magnesium stearate), emulsifiers, oils and fats, especially of plant origin (for example, peanut oil, castor oil, olive oil, sesame oil, cottonseed oil, corn oil, wheat germ oil, sunflower seed oil, cod-liver oil), mono-, di- and triglycerides of saturated fatty acids ($C_{12}H_{24}O_2$ to $C_{18}H_{36}O_2$ and their mixtures), e.g., glyceryl monostearate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400 and other polyethylene glycols, as well as derivatives of such alcohols and polyglycols, esters of saturated and unsaturated fatty acids (2 to 22 carbon atoms, especially 10 to 18 carbon atoms), with monohydric aliphatic alcohols (1 to 20 carbon atom alkanols) or polyhydric alcohols such as glycols, glycerine, diethylene glycol, pentaerythritol, sorbitol, mannitol, ethyl alcohol, butyl alcohol, octadecyl alcohol, etc., e.g., glyceryl stearate, glyceryl palmitate, glycol distearate, glycol dilaurate, glycol diacetate, monoacetin, triacetin, glyceryl oleate, ethylene glycol stearate; such esters of polyvalent alcohols can in a given case also be etherified, benzyl benzoate, dioxolane, glycerine formal, tetrahydrofurfuryl alcohol, polyglycol ethers with 1 to 12 carbon atom alcohols, dimethyl acetamide, lactamide, lactates, e.g., ethyl lactate, ethyl carbonate, silicones (especially middle viscosity dimethyl polysiloxane), magnesium carbonate and the like.

For the production of solutions there can be used water or physiologically compatible organic solvents, as for example, ethanol, 1,2-propylene glycol, polyglycols, e.g., diethylene glycol, triethylene glycol and dipropylene glycol and their derivatives, dimethyl sulfoxide, fatty alcohols, e.g., stearyl alcohol, cetyl alcohol, lauryl alcohol and oleyl alcohol, triglycerides, e.g., glyceryl oleate, glyceryl stearate, glyceryl palmitate, and glyceryl acetate, partial esters of glycerine, e.g., monoacetic, diacetin, glyceryl monostearate, glyceryl distearate, glyceryl monopalmitate, paraffins and the like.

In the production of the preparations there can be used known and customary solution aids or emulsifiers. As solution aids and emulsifiers there can be used, for example, polyvinyl pyrrolidone, sorbitan fatty acid esters such as sorbitan trioleate, lecithin, gum acacia, gum tragacanth, polyoxyethylated sorbitan monoleate, polyoxyethylated fats, polyoxyethylated oleotriglycerides, linolized oleotriglycerides, polyethylene oxide-condensation products of fatty alcohols, alkylphenols or fatty acids. As used herein polyoxyethylated means that the materials in question contain polyoxyethylene chains whose degree of polymerization generally is between 2 and 40, particularly between 10 and 20.

Such polyoxyethylated materials for example can be obtained by reaction of hydroxyl group containing compounds (for example, mono- or diglycerides) or unsaturated compounds such as, for example, those containing the oleic acid radical with ethylene oxide (for example, 40 moles of ethylene oxide per mole of glyceride).

Examples of oleotriglycerides are olive oil, peanut oil, castor oil, sesame oil, cottonseed oil, corn oil (see also Dr. H. P. Fiedler, supra, pages 191-195).

Furthermore, there can be added preservatives, stabilizers, buffers, for example, calcium hydrogen phosphate, colloidal aluminum hydroxide, taste correctives, antioxidants and complex formers (for example, ethylene diamine tetraacetic acid) and the like. In a given case for stabilization of the active molecule the pH is adjusted to about 3 to 7 with physiologically compatible acids or buffers. Generally, there is preferred as neutral as possible to weak acid (to pH 5) pH value. As antioxidants there can be used for example sodium metal bisulfite, ascorbic acid, gallic acid, alkyl gallates, e.g., methyl gallate and ethyl gallate, butyl hydroxyanisole, nordihydroguararetic acid, tocopherols as well as tocopherol and synergists (materials which bind heavy metals by complex formation, for example, lecithin, ascorbic acid, phosphoric acid). The addition of synergists increases considerably the antioxidant activity of tocopherol. As preservatives there can be used for example sorbic acid, p-hydroxybenzoic acid esters (for example, lower alkyl esters such as the methyl ester and the ethyl ester) benzoic acid, sodium benzoate, trichloroisobutyl alcohol, phenol, cresol, benzethonium chloride and formalin derivatives).

The pharmacological and galenical treatment of the compounds of the invention takes place according to the usual standard methods. For example, the active material or materials and assistants or carriers are well mixed by stirring or homogenization (for example, by means of a colloid mill or ball mill), wherein the operation is generally carried out at temperatures between 20° and 80° C., preferably 20° to 50° C.

The application of active material or drug can take place on the skin or mucous membrane or internally, for example, orally, enterally, pulmonarily, rectally, nasally, vaginally, lingually, intravenously, intraarterially, intracardially, intramuscularly, intraperitoneally, intracutaneously or subcutaneously.

The addition of other medicines, especially cardiac glycosides, xanthines, retarders of the aggregation of thrombocytes, nicotinic acid, etc., is also possible or favorable.

The compounds of the invention on narcotized mongrel dogs showed a strong and persistent increase of the peripheral blood flow (circulation) which was determined with electromagnetic flow measuring apparatus. Simultaneously the heart time volume (cold dilution method) was noticeably increased. For example, with the above-mentioned test methods at a dosage of 0.1 mg/kg body weight dog on the average during one hour the circulation of the arteria femoralis increased about 47%. The heart time volume increased in the test on an hourly average about 39%. This vasodilating activity is comparable to the activity of the known medicine, Isoxsuprine.

The lowest vasodilating effective dosage in the above mentioned animal experiment is 0.05 mg/kg intravenously, for example, 1 mg/kg orally; 0.05 mg/kg intravenously.

As the general dosage range for the vasodilating activity (animal experiments as above) there can be used for example 1 to 30 mg/kg orally, particularly 10 mg/kg, 0.1 to 3.0 mg/kg intravenously, particularly 0.3 mg/kg.

The compounds of the invention are indicated for use in disturbances of the peripheral circulation such as Morbus Raynaud, arteriosclerotic vaso illnesses, Ulcus cruris Claudicatio intermittent, diabetic angiopathy, apoplexy and post apoplectic conditions, old age conditioned tropic disturbances as well as hypertonia, particularly in combination with diuretica.

The pharmaceutical preparations generally contain between 5 to 50 mg of the active component or components of the invention.

The compounds can be delivered in the form of tablets, capsules, pills, dragees, plugs, salves, gels, creams, powders, dusts, aerosols or in liquid form. As liquid forms there can be used for example oily or alcoholic or aqueous solutions as well as suspension and emulsions. The preferred forms of use are tablets which contain between 10 and 50 mg or solutions which contain between 1 and 5% of active material.

In individual doses the amount of active component of the invention can be used for example in an amount of:

a. in oral dispensation between 10 and 50 mg;
b. in parenteral dispensation (for example intravenously, intramuscularly) between 5 and 20 mg;
c. in dispensation by inhaling (solutions or aerosols) between 3 and 10 mg.

For example, there is recommended the use of 1 to 3 tablets contaning 20 and 100 mg of active ingredient 3 times daily or for example, intravenously the injection 1 to 3 times daily of a 1 to 10 ml ampoule containing 3 to 30 mg of active substance. In oral preparations the minimum daily dosage for example is 50 mg; the maximum daily dosage in oral administration should not be over 2 grams.

The dosages in each case are based on the free base.

In veterinary medicine the compounds of the invention can be used in treating dogs and cats. The individual dosages in general orally are between approximately 5 and 20 mg/kg body weight; the parenteral dosage approximately between 0.3 and 1.0 mg/kg body weight.

The acute toxicity of the compounds of the invention in the mouse (expressed by the $LD_{50}$ mg/kg method of Miller and Tainter, Proc. Soc. Exper. Biol. and Med. 57 (1944), pages 261 et seq.) in oral application is between 200 mg/kg and 800 mg/kg, in some cases even above 1,000 mg/kg.

The drugs can be used in human medicine, in veterinary medicine as well as in agriculture alone or in admixture with other pharmacologically active materials.

Unless otherwise indicated all parts and percentages are by weight.

The compositions can comprise, consist essentially of or consist of the materials set forth.

The methods can comprise, consist essentially of or consist of the steps set forth with the materials shown.

DESCRIPTION OF THE PREFERRED EMBODIMENTS

The invention is illustrated by the following Examples.

EXAMPLE 1

[1,1-Dithien-(3)-yl-1-hydroxy-(3)-propyl]-[1-hydroxy-1(p-hydroxyphenyl)-(2)-propyl]-amine 25 g (0.15 mole) of p-hydroxy norephedrine, 22.5 ml of triethylamine and 45.5 g (0.15 mole) of 1,1-dithien-(3)-yl-3-bromo-(1)-propanol were heated with stirring for 8 hours to 100° C. in 80 ml of dioxane. The mixture was then largely concentrated in a rotary evaporator, 150 ml of water were added to the residue which was then extracted by shaking three times with 100 ml of diethyl ether. The combined ethereal extracts are dried with magnesium sulfate. After a few hours at 0° C., a pale colored substance crystallized out and was recrystallized from acetone. 15 g of colorless crystalline substance were obtained. M.P.: 174°–175° C.

HYDROGEN MALEATE

To prepare this salt, 5.0 g of the base were suspended in 30 ml of ethylacetate. Following the addition of 1.5 g of maleic acid, a clear solution was formed to which diethyl ether was added until it just began to cloud. After standing for 12 hours, the crystallizate was filtered off under suction, washed with ethylacetate and dried: yield 4.0 g of hydrogen maleate. M.P.: 108°–109° C.

Production of the corresponding starting material 1,1-dithien-(3)-yl-3-bromo-(1)-propanol:

In a 1.5 liter four-necked flask equipped with a dropping funnel, a drying tube, a stirrer, a thermometer and an inlet for nitrogen, 300 ml of absolute diisopropyl ether were cooled under nitrogen with a cooling bath of methanol and dry ice. During cooling, a 15% solution of 335.2 ml of n-butyl lithium in hexane (0.55 mole) was added and the mixture cooled to −75° C. A solution of 81.5 g of 3-bromothiophene (0.5 mole) in 100 ml of absolute diisopropyl ether was then added dropwise over a period of 90 minutes in such a way that a temperature of −70° C. was not exceeded. The reaction mixture was then left to after react for 1 hour at −70° C. to −75° C. A solution of 36.2 g of β-bromopropionic acid ethyl ester (0.2 mole) in 60 ml of absolute diisopropyl ether was then added dropwise over a period of 90 minutes in such a way that the temperature of −70° C. was not exceeded. The reaction mixture was then left to after react for another 4 hours. The cooling bath was then removed and 160 ml of water were added to the reaction mixture. The temperature rises to −20° C. The reaction mixture was then stirred for a while until the temperature had risen above 0° C., after which the organic phase was separated off, dried with MgSO4, filtered and all the low-boiling constituents are distilled off in vacuo in a rotary evaporator. A light oil was obtained as residue. Yield: 54 g (96% of the theoretical, based on the bromopropionic acid ester).

In the same manner there were obtained 1,1-dithienyl-(3)-4-bromo-butanol-(1) and 1,1-dithienyl-(3)-5-bromo-pentanol-(1) in the form of light oils.

EXAMPLE 2

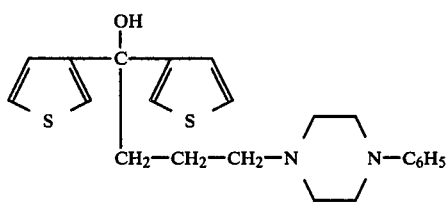

The solution of 16.2 g (0.1 mole) of 4-phenyl piperazine, 14 ml of triethylamine and 31.7 g (0.1 mole) of 1,1-dithienyl-(3)-1-hydroxy-4-bromobutane in 80 ml of diisopropyl ether was allowed to stand for 3 days at room temperature. The crystalline product was filtered off with suction, washed with ether, dried, stirred in water, filtered off with suction, washed with water and dried. The crude yield was 24.4 g, 61.3%.

8 g (0.02 mole) of the crude base were dissolved in 50 ml of acetone. After addition of an acetone solution containing 2.32 g (0.02 mole) of maleic acid, heating and filtering ether was added to the beginning of turbidity. After a short time the material crystallized. This was filtered off with suction, washed with acetone/ether (1:1 by volume) and dried. Yield: 8.3 g (81%). M.P. of the maleate 110°–111° C.

EXAMPLE 3

1,1-Dithienyl-(3)-1-hydroxy-4-[4-(3-methoxyphenyl)-piperazino]-butane

This compound was obtained in an analogous manner to Example 2 using 0.1 mole of 4-(3-methoxyphenyl)-piperazine. M.P. of the maleate: 149°–150° C. (Yield 94%).

EXAMPLE 4

1,1-Dithienyl-(3)-1-hydroxy-5-dimethyl-amino-pentane

The solution of 33 g (0.72 mole) of dimethylamine in 100 ml of benzene and 33.1 g (0.1 mole) of 1,1-dithienyl-(3)-1-hydroxy-5-bromopentane was allowed to stand in a closed reaction vessel for 10 days at room temperature.

Then the crystal mass was filtered off with suction and dried. After concentration of the solution and addition of ether to the residue the crystalline product precipitated out. This was filtered off with suction, dried, combined with the first product obtained and then slurried in water, filtered off with suction, washed with water and dried.

The crude yield was 23.3 g (78%). M.P. 129°–130° C.

10 g of base (0.0338 mole) were slurried in 30 ml of acetone. After addition of 4 g of maleic acid there was formed a clear solution. Ether was added to the beginning of turbidity whereupon after 30 days the substance crystallized.

After filtering off with suction, washing with acetone/ether (1:1 by volume) and drying there were obtained 11.5 g (82% of the title material) of the maleate of the title material, M.P. 79°–80° C.

EXAMPLE 5

Production of Addition [1,1-Dithienyl-(3)-1-hydroxypropyl-(3)]-amines of the formula

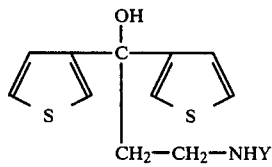

The meaning of —NHY is given in Table 1 column 2.

The compounds entered in Table 1 were produced according to the following procedure:

0.1 mole of 1,1-dithienyl-(3)-3-bromopropanol-(1), 0.11 mole of triethylamine and 0.1 mole of primary or secondary amine (see column 2 of Table 1) were heated at reflux in 60 ml of diisopropyl ether for about 12–15 hours with stirring. After cooling the crystallizate was filtered off with suction, washed with diisopropyl ether and dried. Then it was slurried in water, filtered off with suction, washed with water, dried, recrystallized and analogous to Example 1 there was optionally produced the maleic acid salt.

TABLE 1

| Compound No. D | Amine Component —NHY | Salt | Solvent from Which the Salt was Recrystallized | M.P. of the Salt or Base (°C.) | Yield (%) |
|---|---|---|---|---|---|
| 13564 | —N(piperazine)—C6H4—OCH3 | Maleate | Ethanol/Ether | 140–141° | 51 |
| 13633 | —N(piperazine)—CH2—CH2—C6H5 | Bis-hydrogen-maleate | Ethanol/Ether | 180–181° | 42 |
| 13632 | —N(piperazine)—CH2—C6H5 | Bis-hydrogen-maleate | Ethanol/Ether | 186–187° | 45 |

TABLE 1-continued

| Compound No. D | Amine Component —NHY | Salt | Solvent from Which the Salt was Recrystallized | M.P. of the Salt or Base (°C.) | Yield (%) |
|---|---|---|---|---|---|
| 13637 | —N(piperazine)N—C₆H₄—OCH₃ | Maleate | Methanol/Ether | 130–131° | 39.9 |
| 13774 | —N(piperazine)N—CH₃ | Bis-hydrogen-maleate | Methanol | 179–180° | 38.6 |
| 13834 | —NH—CH(CH₃)₂ | Maleate | Acetone | 154–155° | 23 |
| 13864 | —NH—(CH₂)₃—N(C₂H₅)₂ | Bis-hydrogen maleate | Acetone/Ether | 140–142° | 35 |
| 13895 | —N(piperazine)N—CH₂—CH₂—OH | Bis-hydrogen-maleate | Methanol | 154–155° | 27 |
| 13941 | —NH—C(CH₃)₃ | Maleate | Methanol | 204–206° | 31.5 |
| 14020 | NH—CH(CH₃)—CH(OH)—C₆H₄—OH | — | Methanol | 165–166° (Base) | 42 |
| 14055 | —NH—(CH₂)₃—N(morpholine)O | Bis-hydrogen-maleate | Isopropanol | 144–150° | 25 |
| 14068 | —NH—(cyclohexyl) | Maleate | Acetone | 147–150° | 47 |

EXAMPLE 6

[1,1-Dithien-(3)-yl-1-propen-(3)-yl]-[1-hydroxy-1-(p-hydroxyphenyl)-(2)-propyl]-amine 25 g (0.15 mole) of p-hydroxy norephedrine, 22.5 ml of triethylamine and 45.5 g (0.15 mole) of 1,1-dithien-(3)-yl-3-bromo-(1)-propanol were heated with stirring for 8 hours to 100° C. in 80 ml of dioxane. The mixture was then substantially concentrated in a rotary evaporator and the syrupy residue was digested twice with 250 ml of diethyl ether. The combined ethereal solutions were acidified with isopropanolic HCl, as a result of which a highly viscous product precipitated. After the solvent was poured off, the residue was taken up in 100 ml of ethanol, followed by boiling under reflux for 10 minutes. The solution was then concentrated in a rotary evaporator. The residue was dissolved in 100 ml of warm acetone from which the substance slowly crystallized out after cooling. Recrystallization from isopropanol gave the hydrochloride of the compound in the form of colorless crystals. M.P. of the hydrochloride: 138°–140° C. Yield: 10.2 g.

EXAMPLE 7

Production of 1,1-Dithienyl-(3)-alken-(1)-yl-amines of the Formula

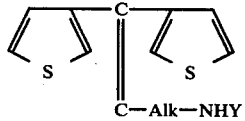

The meanings of NHY and Alk are given in Table 2.
The compounds entered in Table 2 were produced according to the following procedure:
0.1 mole of an amine of the formula

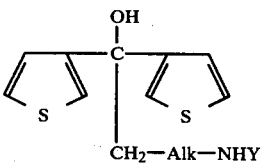

(the meanings of NHY and Alk are given in Table 2) was dissolved in 50 ml of methanol and treated with a 10% excess of the amount necessary to form the salt of isopropanolic hydrochloric acid whose concentration was 5–7 moles per liter. The reaction mixture was heated for about 20–30 minutes under reflux. After cooling the various compounds crystallized out. If this occasionally is not the case then the solutions are treated with sufficient ether that a lasting turbidity occurs; the reaction product there separates out, usually in crystalline form.

The solvents for recrystallization are preferably methanol, ethanol and isopropanol.

TABLE 2

| Compound No. D | Amine Component —NHY | Alk | Salt | Solvent from Which the Salt was Recrystallized | M.P. of the Salt (°C.) | Yield (%) |
|---|---|---|---|---|---|---|
| 13565 | —N(piperazine)N—C₆H₄(2-OCH₃) | —CH₂— | 2 HCl | Methanol (Ether) | 215–217° decomposition | 78.8 |
| 13631 | —N(piperazine)N—C₆H₄(4-F) | —CH₂— | 2 HCl | Methanol | 188–189° decomposition | 85.5 |
| 13630 | —N(piperazine)N—C₆H₄(4-OCH₃) | —CH₂— | 2 HCl | Isopropanol | 218–219° | 71.9 |
| 13629 | —N(piperazine)N—C₆H₃(2,3-(CH₃)₂) | —CH₂— | 2 HCl | Methanol | 215–216° | 40 |
| 13635 | —N(piperazine)N—CH₂—C₆H₅ | —CH₂— | 2 HCl | Methanol | 244–245° | 90.4 |
| 13634 | —N(piperazine)N—CH₂—CH₂—C₆H₅ | —CH₂— | 2 HCl | Methanol | 270° (decomposition) | 98 |
| 13636 | —N(piperazine)N—C₆H₄(2-OC₂H₅) | —CH₂— | 2 HCl | Methanol | 228–229° | 33 |
| 13719 | —N(piperazine)N—C₆H₅ | —CH₂— | 2 HCl | Methanol | 194–195° | 42 |
| 13724 | —N(piperazine)N—CH₂—C₆H₂(2,3,4-(OCH₃)₃) | —CH₂— | 2 HCl | Methanol | 220° decomposition | 63 |
| 13737 | —N(piperazine)N—C₆H₄(2-CH₃) | —CH₂— | 2 HCl | Methanol/Ether | 185–187° | 54 |
| 13833 | —NH—CH₂—C₆H₂(2,3,4-(OCH₃)₃) | —CH₂— | 2 HCl | Isopropanol/Ether | 160–161° | 65 |
| 13835 | —NH—CH(CH₃)₂ | —CH₂— | HCl | Isopropanol/Ether | 142–143° | 56 |
| 13863 | —NH—CH₂—C₆H₃(3,4-OCH₂O—) | —CH₂— | HCl | Isopropanol/Ether | 169–170° | 90 |
| 13866 | —NH—(CH₂)₃—N(C₂H₅)₂ | —CH₂— | 2 HCl | Isopropanol/Ether | 145–146° | 78.5 |
| 13897 | —NH—CH₂—C₆H₃(2,3-(OCH₃)₂) | —CH₂— | HCl | Methanol/Ether | 137–138° | 72 |
| 14003 | —NH—(CH₂)₃—N(piperazine)N—CH₃ | —CH₂— | 3 HCl | Methanol | 250–252° | 56 |
| 14057 | —NH—cyclohexyl | —CH₂— | HCl | Methanol | 204–207° decomposition | 48.5 |
| 14094 | —NH—CH(cyclopropyl) | —CH₂— | HCl | Isopropanol/Ether | 188–191° | 67 |

TABLE 2-continued

| Compound No. D | Amine Component —NHY | Alk | Salt | Solvent from Which the Salt was Recrystallized | M.P. of the Salt (°C.) | Yield (%) |
|---|---|---|---|---|---|---|
| 13661 | —N(morpholine)O | —(CH$_2$)$_2$— | HCl | Ethanol/Ether | 182–183° | 46.9 |
| 13662 | —N(piperidine) | —(CH$_2$)$_2$— | HCl | Ethanol/Ether | 175–176° | 38 |
| 13678 | —NH—CH(CH$_3$)—CH(OH)—C$_6$H$_5$ | —(CH$_2$)$_2$— | HCl | Methanol/Ether | 183–184° | 15 |
| 13685 | —NH—CH$_3$ | —(CH$_2$)$_2$— | HCl | Acetone/Ether | 155–156° | 35 |
| 13682 | —N(piperazine)N—C$_6$H$_4$(OCH$_3$) | —(CH$_2$)$_2$— | 2 HCl | Methanol/Ether | 212–213° | 30 |
| 13686 | —N(piperazine)N—C$_6$H$_5$ | —(CH$_2$)$_2$— | 2 HCl | Methanol | 216–217° decomposition | 49 |
| 13705 | —N(CH$_3$)$_2$ | —(CH$_2$)$_2$— | HCl | Methanol/Ether | 143–144° | 59 |
| 13800 | —NH—CH(CH$_3$)—CH(OH)—C$_6$H$_4$—OH | —(CH$_2$)$_2$— | HCl | Methanol | 210–211° | 68 |
| 13775 | —NH—CH(CH$_3$)—CH(OH)—C$_6$H$_5$ | —(CH$_2$)$_3$— | HCl | Ethanol | 191–192° | 26 |
| 13786 | —N(piperazine)N—C$_6$H$_4$(OCH$_3$) | —(CH$_2$)$_3$— | 2 HCl | Methanol/Ether | 203–204° decomposition | 28 |
| 13799 | —N(piperazine)N—C$_6$H$_5$ | —(CH$_2$)$_3$— | 2 HCl | Methanol | 225–226° decomposition | 28 |
| 13861 | —NH—CH(CH$_3$)—CH(OH)—C$_6$H$_4$—OH | —(CH$_2$)$_3$— | HCl | Methanol/Ether | 177–178° | 15 |

EXAMPLE 8 (Capsules)

To prepare 500,000 capsules there were required the following raw materials:

| | | |
|---|---|---|
| I. | D 13565 compound (see Table 2) | 10.0 kg |
| | Lactose | 60.0 kg |
| | Microcrystalline cellulose | 58.8 kg |
| | Magnesium stearate | 1.2 kg |
| | | 130.0 kg |
| II. | 500,000 gelatin capsules, size 2 | |

PRODUCTION (1) D 13,565 compound was comminuted to such an extent in an air jet mill equipped with a dust shield that the particles had the following particle size:

| at least 50% | not over 5μ |
|---|---|
| the remainder | not over 10μ |

This comminuted compound is identified below as micronized D 13,565 compound.

(2) The total raw materials which were necessary for production of the capsule composition were passed through a sieve having a mesh width of 1.5 mm. Then 58.8 kg of micronized cellulose and 10 kg of micronized D 13,565 compound were mixed for 1 hour at 10 revolutions per minute in a Turbula mixer. Subsequently, the mixture was treated with 60 kg of lactose and 1.2 kg of magnesium stearate and again mixed for 45 minutes. This composition is called the capsule filling composition.

(3) The capsule filling composition was filled into gelatin capsules of size 2.

Amount of filling per capsule: 260 mg.

EXAMPLE 9 (Suppositories)

Production 20 g of D 13,565 compound were worked into 1980 g of molten suppository composition (for example, hard fat DAB 7) and in known manner poured out in forms for 2.0 g suppositories.

1 suppository contains 20 mg of D 13,565 compound.

What is claimed is:

1. A compound of the formula

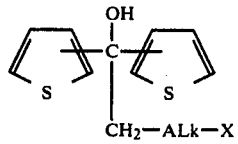

where Alk is $CH_2$ and X is chlorine, bromine or iodine.

2. A compound according to claim 1 wherein X is bromine.

* * * * *